United States Patent
Foody et al.

(10) Patent No.: US 7,670,813 B2
(45) Date of Patent: *Mar. 2, 2010

(54) INORGANIC SALT RECOVERY DURING PROCESSING OF LIGNOCELLULOSIC FEEDSTOCKS

(75) Inventors: Brian Foody, Ottawa (CA); Jeffrey S. Tolan, Ottawa (CA); Ziyad Rahme, Ottawa (CA); Vijay Anand, Brossard (CA)

(73) Assignee: Iogen Energy Corporation, Ontario (CA)

( * ) Notice: Subject to any disclaimer, the term of this patent is extended or adjusted under 35 U.S.C. 154(b) by 443 days.

This patent is subject to a terminal disclaimer.

(21) Appl. No.: 11/586,135

(22) Filed: Oct. 25, 2006

(65) Prior Publication Data

US 2008/0102502 A1 May 1, 2008

(51) Int. Cl.
*C12P 19/02* (2006.01)
*C12P 3/00* (2006.01)
*C12P 7/06* (2006.01)
*C12P 7/08* (2006.01)

(52) U.S. Cl. .................. 435/105; 435/161; 435/163; 435/164; 435/168; 127/37; 127/39; 127/42

(58) Field of Classification Search .............. None
See application file for complete search history.

(56) References Cited

U.S. PATENT DOCUMENTS

| | | | |
|---|---|---|---|
| 4,048,341 A | 9/1977 | Lagerstrom et al. | |
| 4,101,338 A | 7/1978 | Rapaport et al. | |
| 4,237,226 A | 12/1980 | Grethlein | |
| 4,321,360 A | 3/1982 | Blount | |
| 4,356,196 A | 10/1982 | Hultquist | |
| 4,461,648 A | 7/1984 | Foody | |
| 4,556,430 A | 12/1985 | Converse et al. | |
| 4,600,590 A | 7/1986 | Dale | |
| 4,644,060 A | 2/1987 | Chou | |
| 5,037,663 A | 8/1991 | Dale | |
| 5,124,004 A | 6/1992 | Grethlein et al. | |
| 5,171,592 A | 12/1992 | Holtzapple et al. | |
| 5,177,008 A | 1/1993 | Kampen | |
| 5,536,325 A | 7/1996 | Brink | |
| 5,620,877 A | 4/1997 | Farone et al. | |
| 5,782,982 A | 7/1998 | Farone et al. | |
| 5,789,210 A | 8/1998 | Ho et al. | |
| 5,865,898 A | 2/1999 | Holtzapple et al. | |
| 5,932,456 A | 8/1999 | Van Draanen et al. | |
| 5,939,544 A | 8/1999 | Karstens et al. | |
| 6,043,392 A | 3/2000 | Holtzapple et al. | |
| 6,106,888 A | 8/2000 | Dale et al. | |
| 6,176,176 B1 | 1/2001 | Dale et al. | |
| 6,478,965 B1 | 11/2002 | Holtzapple et al. | |
| 6,589,760 B1 | 7/2003 | Buchanan et al. | |
| 6,608,184 B2 | 8/2003 | Blount | |
| 6,709,527 B1 | 3/2004 | Fechter et al. | |
| 7,585,652 B2 * | 9/2009 | Foody et al. .............. 435/163 |

FOREIGN PATENT DOCUMENTS

WO WO 02/18610 3/2002
WO WO 2005099854 A1 * 10/2005

OTHER PUBLICATIONS

ASL-Clemson, Agricultural Service laboratory, Plant Tissue Analysis, Clemson Extension; Guidelines for Sampling and Interpreting Results, Accessed May 1, 2006.

Bailar, J.C., Jr., Comprehensive Inorganic Chemistry; 1973, ISBN 00807175, Compendium Publishers New York.

Dien, B.S., et al., "Conversion of corn milling fibrous co-products into ethanol by recombinant . . . ," World Journal of Microbiology & Biotechnology 13:619-625 (1997).

Fontana, J.D., et al., "Cassava Starch Maltodextrinization/Monomerization Through Thermopressurized . . . ," Applied Biochemistry and Biotechnology V91-93:469-489 (2001).

Larsson, M., et al., "Recirculation of Process Water in the Production of Ethanol From Softwood," Bioresource Technology 60:143-151 (1997).

Pessoa, A., Jr., et al., "Acid Hydrolysis of Hemicellulose From Sugarcane Bagasse," Brazilian Journal of Chemical Engineering 14:291-297 (1997).

(Continued)

*Primary Examiner*—Herbert J. Lilling
(74) *Attorney, Agent, or Firm*—Fitzpatrick, Cella, Harper & Scinto

(57) ABSTRACT

A method for recovering inorganic salt during processing of a lignocellulosic feedstock is provided. The method comprises pretreating the lignocellulosic feedstock by adding an acid or a base to the feedstock to produce a pretreated lignocellulosic feedstock. A soluble base or acid is then added to the pretreated lignocellulosic feedstock to adjust the pH and produce a neutralized feedstock. The neutralized feedstock is then hydrolyzed to produce an hydrolyzed feedstock and a sugar stream. Inorganic salt is recovered from a wash stream obtained from the pretreated lignocellulosic feedstock, a stream obtained from the neutralized feedstock, a stream obtained from the sugar stream, or a combination of these streams. The inorganic salt may be concentrated, clarified, recovered and purified by crystallization, electrodialysis, drying, or agglomeration and granulation, and then used as desired, for example, as a fertilizer.

37 Claims, 1 Drawing Sheet

OTHER PUBLICATIONS

Ruthven, D.M. (Editor) Encyclopedia of Separation Technology, May 1997.

Schell, D.J., et al., "Dilute-Sulfuric Acid Pretreatment of Corn Stover in Pilot-Scale Reactor," Applied Biochemistry and Biotechnology 105-108:69-85(2003).

Shambe, T., et al., "Acid and Enzymic Hydrolysis of Chaotropically Pretreated Millet Stalk, Acha and Rice Straws . . .," Enzyme Microb. Techol. 7:115-120 (1985).

Shriver, D., et al., "Inorganic Chemistry, Third Edition," Jan. 1999.

Thompson, D.N., et al, "Post-Harvest Processing Methods for Reductio of Silica and Alkali Metals . . . ," Applied Biochemistry and Biotechnology 105-108:205-218 (2003).

Wooley, R., et al., "Lignocellulosic Biomass to Ethanol Process Design and Economics Utilizing . . . ," Technical Report, National Renewable Energy Lab.pp. 16-17(1999).

Wyman, C.E., "Biomass Ethanol: Technical Progress, Opportunities, and Commercial Challenges," Annu. Rev. Energy Environ 24:189-226 (1999).

Lee, et al., "Recovery of ammonium sulfate from fermentation waste by electrodialysis", Water Research, vol. 37 (2003) 1091-99.

Cao, et al., "Ethanol Production From Corn Cob Pretreated by the Ammonia Steeping Process Using Genetically Engineered Yeast", Biotechnology Letters, vol. 18, No. 9 (1996) 1013-18.

* cited by examiner

INORGANIC SALT RECOVERY DURING PROCESSING OF LIGNOCELLULOSIC FEEDSTOCKS

STATEMENT REGARDING FEDERALLY SPONSORED RESEARCH OR DEVELOPMENT

Not applicable

FIELD OF INVENTION

The present invention relates to a method for processing lignocellulosic feedstocks. More specifically, the present invention provides a method for recovering inorganic salt during the processing of lignocellulosic feedstocks.

BACKGROUND OF THE INVENTION

Fuel ethanol is currently made from feedstocks such as corn starch, sugar cane, and sugar beets. The production of ethanol from these sources cannot grow much further, as most of the farmland suitable for the production of these crops is in use. In addition, these feedstocks can be costly since they compete with the human and animal food chain. Finally, the use of fossil fuels, with the associated release of carbon dioxide and other products, for the conversion process is a negative environmental impact of the use of these feedstocks.

The production of fuel ethanol from cellulosic feedstocks provides an attractive alternative to the fuel ethanol feedstocks used to date. Cellulose is the most abundant natural polymer, so there is an enormous untapped potential for its use as a source of ethanol. Cellulosic feedstocks are also inexpensive, as they do not have many other uses. Another advantage of producing ethanol from cellulosic feedstocks is that lignin, which is a byproduct of the cellulose conversion process, can be used as a fuel to power the conversion process, thereby avoiding the use of fossil fuels. Several studies have concluded that, when the entire cycle is taken into account, the use of ethanol produced from cellulose generates close to nil greenhouse gases.

The cellulosic feedstocks that are the most promising for ethanol production include (1) agricultural wastes such as corn stover, wheat straw, barley straw, canola straw, rice straw, and soybean stover; (2) grasses such as switch grass, miscanthus, cord grass, and reed canary grass, (3) forestry wastes such as aspen wood and sawdust, and (4) sugar processing residues such as bagasse and beet pulp.

Regardless of the feedstock used, the first step involves handling and size reduction of the material. The feedstock must be conveyed into the plant. This is contemplated to be carried out by trucks, followed by placing the feedstock on conveyor belts to be conveyed into the plant. The feedstock particles must then be reduced to the desired size to be suitable for handling in the subsequent processing steps.

The first process step is a chemical treatment, which generally involves the use of steam or heated water along with acid or alkali to break down the fibrous material. The chemical treatment is carried out either as a direct conversion process-acid hydrolysis or alkali hydrolysis- or as a pretreatment prior to enzymatic hydrolysis.

In the acid hydrolysis process, the feedstock is subjected to steam and sulfuric acid at a temperature, acid concentration, and length of time that are sufficient to hydrolyze the cellulose to glucose and hemicellulose to xylose and arabinose. The sulfuric acid can be concentrated (25-90% w/w) or dilute (3-8% w/w). The glucose, xylose and arabinose are then fermented to ethanol using yeast, and the ethanol is recovered and purified by distillation. A problem with concentrated acid hydrolysis is that the high levels of concentrated acid required necessitate the recovery and re-use of over 99% of the acid in the process. The recovery of this high proportion of acid is especially difficult due to the high viscosity and corrosivity of concentrated acid.

In the alkali hydrolysis process, the feedstock is subjected to steam and sodium hydroxide or potassium hydroxide at a temperature, concentration, and length of time that are sufficient to hydrolyze the cellulose to glucose and hemicellulose to xylose and arabinose. The alkali is concentrated (15-50% w/w). The glucose, xylose and arabinose are then fermented to ethanol using yeast, and the ethanol is recovered and purified by distillation. A problem with alkali hydrolysis is that the high levels of alkali required necessitate the recovery and re-use of over 99% of the alkali in the process. The recovery of this high proportion of alkali is especially difficult due to the high viscosity of concentrated alkali.

In the enzymatic hydrolysis process, the feedstock is first pretreated with acid or base under milder conditions than that in the acid or alkali hydrolysis processes such that the exposed cellulose surface area is greatly increased as the fibrous feedstock is converted to a muddy texture. During acid pretreatment, much of the hemicellulose is hydrolyzed, but there is little conversion of the cellulose to glucose. The cellulose is hydrolyzed to glucose in a subsequent step that uses cellulase enzymes, and the steam/acid treatment in this case is known as pretreatment. The acids used in pretreatment typically include sulfuric acid in steam explosion and batch and continuous flow pretreatments and also sulfurous acid and phosphoric acid.

Some alkali pretreatment methods disclosed in the prior art, such as those involving concentrated ammonia, do not hydrolyze hemicellulose, but rather the base reacts with acidic groups present on the hemicellulose to open up the surface of the substrate. In addition, the concentrated ammonia alters the crystal structure of the cellulose so that it is more amenable to hydrolysis. Examples of such bases typically used in pretreatment include ammonia or ammonium hydroxide. The cellulose is hydrolyzed to glucose in a subsequent step that uses cellulase enzymes, although it is also possible to hydrolyze the cellulose, in addition to the hemicellulose, using acid hydrolysis after alkaline pretreatment.

The hydrolysis of the cellulose, whether by acid or alkali hydrolysis or by cellulase enzymes after pretreatment with acid or base, is followed by the fermentation of the sugar to ethanol. The ethanol is then recovered by distillation.

There are several problems that must be overcome in order for the conversion of cellulosic biomass to sugar or ethanol to be commercially viable. In particular, there is a large amount of inorganic salt present in the feedstock. Furthermore, inorganic salt is generated in the process, in particular, during the neutralization of the acid or alkali used in the pretreatment or hydrolysis. The inorganic salt has an adverse impact on the enzymatic hydrolysis and yeast fermentation processes. In addition, the purchase of the acid and the alkali and the disposal of the salt are costly.

If the pretreated feedstock is subjected to enzymatic hydrolysis by cellulase enzymes, the pH of the pretreated feedstock is typically between about 4-6. Cellulase enzymes produced by the fungus *Trichoderma*, which are the leading sources of cellulase for cellulose conversion, exhibit optimum activity at pH 4.5 to 5.0. These enzymes exhibit little activity below pH 3 or above pH 6. Microbes that ferment the sugar include yeast and *Zymomonas* bacteria. The yeast are active at pH 4-5 while the *Zymomonas* are active at pH 5-6. An acidic chemical treatment is often carried out at a pH of about 0.8 to 2.0, so a significant amount of alkali must be added to increase the pH to the range that is required for microbial fermentation and enzymatic hydrolysis. An alkaline pretreatment is often carried out at a pH of 9.5 to 12, so a significant amount of acid must be added to decrease the pH to the range that is required for enzymatic hydrolysis and microbial fermentation.

When an acidic pretreatment is carried out, the alkaline that is usually used for neutralization of the acid is sodium hydroxide, but potassium hydroxide and ammonium hydroxide have also been reported. The high levels of these compounds that are required increase the cost of the process.

Although the neutralized slurry is at a pH range that is compatible with yeast or fermenting bacteria or cellulase enzymes, the inorganic salt concentration is high enough to be inhibitory to the microbes or enzymes. The inorganic salt can also cause a degradation of the sugar, particularly the xylose, in evaporation and distillation processes that are carried out downstream of the hydrolysis.

One known pretreatment method utilizing a base is known as Ammonia Freeze Explosion, and more recently as the Ammonia Fiber Explosion or "AFEX" process. The process involves contacting lignocellulosic feedstock with liquid ammonia in a pressure vessel. The contact is maintained for a sufficient time to enable the ammonia to swell (i.e., decrystallize) the cellulose fibers, and the pressure is then rapidly reduced which causes the ammonia to flash or boil and explode the cellulose fiber structure. (See U.S. Pat. Nos. 5,171,592, 5,037,663, 4,600,590, 6,106,888, 4,356,196, 5,939,544, 6,176,176, 5,037,663 and 5,171,592 which are incorporated herein by reference.)

The AFEX process typically requires the addition of ammonia at high concentrations. Due to the high cost of ammonia, AFEX pretreatment methods involve recovery of the flashed ammonia, which, in turn, is recycled to the pretreatment step. However, the ammonia recovery process does not remove all of the ammonia from the pretreated feedstock. The inability to recover this residual ammonia decreases the economics of the process.

U.S. Pat. No. 4,644,060 discloses a pretreatment method involving contacting lignocellulosic materials with ammonia. This is followed by flashing to recover and re-use the ammonia. The pretreated material is then subjected to enzyme hydrolysis with cellulases. Prior to enzyme hydrolysis, the pH of the pretreated feedstock is neutralized by addition of hydrochloric acid. As a result of the cellulase treatment, most of the available cellulose was hydrolyzed to glucose and 78% of the available xylan was hydrolyzed to xylobiose and xylose. However, a disadvantage of this method is that the ammonia recovery process does not remove all of the ammonia from the pretreated feedstock, which limits the economic viability of the method.

Alkali that is used during processing of the lignocellulosic feedstock can be either soluble or insoluble. An example of an insoluble alkali is lime, which is typically used to neutralize acids and precipitate inhibitors of cellulase enzymes arising from the pretreatment. It is also known to pretreat lignocellulosic feedstocks with hydrated lime (calcium hydroxide). However, there are numerous problems associated with using lime including (1) disposal of the lime; (2) calcium precipitation which leads to downstream scaling; (3) the expense of the lime; and (4) its ineffectiveness at completely removing inhibitors of enzymes and yeast.

Holtzapple (U.S. Pat. No. 5,865,898) discloses an alkaline pretreatment using insoluble hydrated lime (calcium hydroxide). After the alkali pretreatment, the pH is reduced to a pH amenable for enzymatic hydrolysis using acetic acid. The pretreated biomass is digested and useful products such as alcohols, organic acids, sugars, ketones, starches, fatty acids, are separated from the remaining or residual mixture. Calcium hydroxide is recovered by reacting the pretreated material with carbon dioxide to convert it to calcium carbonate. The residual insoluble solids, comprising lignin and calcium carbonate, are heated in a lime kiln to convert the calcium carbonate into calcium hydroxide. However, this is a very expensive and time consuming process that involves handling and processing a large amount of insoluble salts. It has therefore not been possible, to date, for this process to be economically viable.

U.S. Pat. No. 6,043,392 (Holtzapple et al.) employs a pretreatment step with lime prior to producing volatile fatty acids during the fermentation of lignocellulosic biomass by anaerobic or thermophilic bacteria. After the lime treatment, lime is removed by draining the lime-containing water from the biomass, followed by fermentation with anaerobic bacteria. The anaerobic organisms then convert the biomass to organic acids such as acetic acid, proprionic and butyric acids. The organic acids produced by these fermentation processes can be concentrated and converted to ketones by pyrolysis in a thermal converter. Calcium salts can be precipitated by evaporation, dried and pyrolyzed to produce solid calcium carbonate. The calcium carbonate may be sent to a lime kiln to regenerate lime which may then be mixed with water to produce a dissolved lime stream and insolubles. Minerals may be recovered from a side stream of calcium carbonate or from the insolubles and sold as fertilizer. Alternatively, the organic acids are treated with a tertiary amine and carbon dioxide to produce an acid/amine complex that decomposes to form an acid and an amine with different volatilities. The acid can then be separated from the amine by distillation and precipitated minerals that accumulate in the bottoms of the distillation column can be recovered. Although Holtzapple et al. describe an effective method for the isolation of organic acids produced during fermentation using an alkaline pretreatment, the method involves pretreatment with insoluble lime, which is subject to the disadvantages described above.

Alkali treatment of lignocellulosic feedstocks has also been employed to produce animal feed. In this case, the treatment with alkali increases the feed value of the feedstock by making cellulose more accessible to digestion by ruminants. U.S. Pat. No. 4,048,341 discloses such a process for producing animal fodder. After alkali chemical treatment, the lignocellulosic material is treated with acid to neutralize the fodder. However, the process is limited to the production of animal fodder and there is no disclosure of producing a sugar stream.

Wooley et al. (In Lignocellulosic Biomass to Ethanol Process Design and Economics Utilizing Co-Current Dilute Acid Prehydrolysis and Enzyme Hydrolysis Current and Future Scenarios, (1999) Technical Report, National Renewable Energy Laboratory pp. 16-17) describe a process of treating lignocellulosic material utilizing over-liming following acid pretreatment. Milled wood chips are first pretreated with dilute sulfuric acid followed by enzyme hydrolysis and fermentation. Following pretreatment, the resulting liquid and solids are flash cooled to vapourize a large amount of water and inhibitors of the downstream fermentation reaction. After ion exchange to remove acetic acid, the material is over-limed by adding lime to raise the pH to 10. The liquid is then adjusted to pH 4.5 which results in the formation of gypsum crystals ($CaSO_4$). These crystals can be removed from the liquid by hydrocyclone and rotary drum filtration in series. Although the process describes the removal of gypsum after acid treatment, the investigators do not address the problems associated with removal of insoluble calcium salt.

U.S. Pat. No. 6,478,965 (Holtzapple et al.) discloses a method for isolating carboxylate salts formed as a product during the fermentation of lignocellulosic biomass by anaerobic bacteria. A fermentation broth, which contains dilute carboxylate salt in aqueous solution, is contacted with a low molecular weight secondary or tertiary amine which has a high affinity for water and a low affinity for the carboxylate salt. This allows the water to be selectively extracted while the carboxylate salt remains in the fermentation broth and becomes concentrated so that it can be easily recovered. The carboxylate salt may be further concentrated by evaporation, dried or converted to a more concentrated carboxylic acid solution. While Holtzapple et al. describe an effective method for the isolation of carboxylate fermentation products, they do not address the recovery of inorganic salts from the feedstock itself or inorganic salts arising from the acids and bases used during the processing of the lignocellulosic feedstocks.

U.S. Pat. No. 5,124,004 (Grethlein et al.) discloses a method for concentrating an ethanol solution by distillation. The method first involves partially concentrating the ethanol solution by distillation and withdrawing a vapour stream. Next, the condensation temperature of the vapour is raised above the evaporation temperature of a re-boiler liquid used in the process (a heat-sink liquid). The vapour stream is then used to heat the re-boiler liquid and partially enriched vapour is then removed and condensed. The condensed stream is introduced to an extractive distillation column and concentrated in the presence of an added salt to increase the volatility of the ethanol. The method provides the benefit that the heat requirement of distillation is reduced since vapour required to heat the system does not need to be provided by an external source. However, there is no discussion of recovering and removing the salts added during the final distillation step.

U.S. Pat. No. 5,177,008 (Kampen) discloses the recovery of fermentation by-products, namely glycerol, betaine, L-pyroglutamic acid, succinic acid, lactic acid and potassium sulfate, produced during the manufacture of ethanol from sugar beets. The process involves fermenting the raw material, collecting the ethanol by distillation and then recovering the by-products in the remaining still bottoms. The by-products are isolated by first centrifuging the still bottoms and performing microfiltration to further clarify the solution. The resulting permeate is then concentrated to a solids concentration of 50-75%. The concentrated solution is first subjected to a crystallization step to recover potassium sulfate and then passed to a chromatographic separation step for the subsequent recovery of glycerol, betaine, succinic acid, L-pyroglutamic acid or lactic acid. The potassium sulfate is present in the raw material and its concentration is increased by cooling the solution and/or by the addition of sulfuric acid as part of the crystallization. The process of Kampen has several advantages such as energy and water savings and high solids concentrations. However, there is no discussion of a chemical pretreatment of lignocellulosic material with acid or alkali or an acid or alkali neutralization step prior to enzymatic hydrolysis and fermentation and the associated problems with the presence of sodium and magnesium salts arising from such a pretreatment. Furthermore, since Kampen et al. used sugar beets, they were able to crystallize potassium sulfate directly from the still bottoms, and they do not address the recovery from still bottoms of salt mixtures with high levels of impurities that do not crystallize. Acid pretreatment of lignocellulosic feedstocks results in mixtures of inorganic salts in the still bottoms that cannot be directly crystallized.

U.S. Pat. Nos. 5,620,877 and 5,782,982 (Farone et al.) disclose a method for producing sugars from rice straw using concentrated acid hydrolysis which, as set out above, is not a preferred pretreatment method. The method results in the production of quantitative yields of potassium silicate. In this method, the rice straw is treated with concentrated sulfuric acid at a concentration of between 25% and 90%. The resulting mixture is then heated to a temperature to effect acid hydrolysis of the rice straw. Subsequently, the mixture is separated from the remaining solids by pressing. The pressed solids can then be treated with 5% to 10% sodium hydroxide to extract silicic acid. Following the treatment with sodium hydroxide, the solids are heated and then pressed and washed with water to extract a liquid. The extracted liquid is then treated with an acid, which results in the formation of a precipitate that can be separated by filtration. The filtered material is then treated with bleach to produce silica gel that can be further treated to produce sodium silicate, potassium silicate or other useful materials. The method also employs a neutralization step using lime to precipitate soluble inorganic salts present in a sugar stream produced during fermentation. Lime is an insoluble base that can build up on process equipment downstream of its point of addition and decrease the efficiency of the process.

WO 02/070753 (Griffin et al.) discloses a leaching process to remove alkali from lignocellulosic feedstocks thereby decreasing the acid requirement for chemical treatment. The process includes milling the feedstock, followed by preconditioning it with steam and then contacting the feedstock with water to leach out the salts, protein, and other impurities. The water containing these soluble compounds is then removed from the feedstock. This process decreases the acid requirements in the subsequent pretreatment process, which increases the yield of xylose after pretreatment. However, the costs and problems associated with the salt arising from the acid or alkali added for chemical treatment and the alkali or acid added after chemical treatment for adjustment of the pH are not addressed.

U.S. Pat. No. 4,321,360 (Blount) discloses the preparation of ethanol from lignocellulosic feedstocks; however, there is no discussion of salt processing or recovery arising during this process. U.S. Pat. No. 6,608,184 (Blount) describes the production of ethanol, salt, and several other organic products from sewer sludge comprising sewered cellulose waste material (rather than a lignin-cellulose material). This process involves mixing sewer sludge with water and sodium hydroxide, or an acid (sulfuric or hydrochloric acid). The slurry containing acid or alkali is then heated to hydrolyze the cellulose in the sludge, and an excess of water is added to dissolve the organic compounds. The aqueous material is then separated from the insolubles and evaporated to concentrate the solution and crystallize out the carbohydrates. The carbohydrates are filtered off, slurried in water, and fermented to ethanol using yeast. The aqueous solution containing ammonium sulfate and other compounds may then be used as a fertilizer. Alternatively, the salt is separated from the sugar by membrane filtration and then the salt is evaporated and dried.

U.S. Pat. No. 6,709,527 (Fechter et al.) discloses a process of treating an impure cane-derived sugar juice to produce white sugar and white strap molasses. The process involves subjecting the sugar juice to microfiltration/ultrafiltration to decrease the levels of suspended solids, organic non-sugar impurities and/or colour. The sugar juice is next subjected to ion exchange with a strong acid cation exchange resin in the hydrogen form and then to ion exchange with an anion ion exchange resin in the hydroxide form. Potassium-based fertilizer components can be obtained by regenerating the strong acid cation exchange resin with a strong acid such as hydrochloric acid or nitric acid to produce an acid stream rich in potassium salt. Ammonium-based fertilizer components can be obtained by regenerating the anion ion exchange resin with a strong or weak base such as sodium or potassium hydroxide and ammonium hydroxide to obtain an alkaline stream which is rich in nitrogen. After ion exchange, the resulting sugar solution is concentrated to produce a syrup, which is crystallized twice to produce impure crystallized sugar and white strap molasses. Although the process involves the production of potassium and ammonium-based fertilizer components from an impure sugar cane juice, there is no disclosure of producing a sugar stream by hydrolysis of a lignocellulosic feedstock.

U.S. Pat. No. 4,101,338 (Rapaport et al.) disclose the separation of sucrose from impurities in sugar cane molasses. Rapaport et al. teach the pretreatment of a molasses stream to remove a significant amount of organic non-carbohydrate impurities and colour. The pretreatment can be carried out by precipitation with iron salts, such as ferric chloride or ferric sulfate. The insoluble flocculants are then removed from the molasses stream and the soluble iron salts are removed by the addition of lime and phosphoric acid or phosphate salts. The pretreatment may also be carried out by other processes which include: centrifugation, with removal of the cake; precipitation by adding ethanol to the molasses stream; and filtering the molasses across a membrane of cellulose acetate. Regardless of the pretreatment process, the purpose is to decrease the amount of organic non-carbohydrate impurities so that a subsequent step of ion exclusion chromatography will separate the carbohydrate fraction from the dissolved impurities. Rapaport et al. report that the pretreatment decreased the ash content to 10% and the organic non-sugar content to 16.3% of the solids present.

Organic non-carbohydrate impurities, within a lignocellulosic system, cannot be removed by the methods of U.S. Pat. No. 4,101,338 (Rapaport et al.) According to Rapaport's method, the amount of solids precipitated by iron salts or ethanol is modest and no solids are removed by centrifugation. By contrast, the sugar streams produced during the processing of lignocellulosic feedstock have a much higher level of organic non-carbohydrate impurities and inorganic salts. Rapaport et al. do not address the processing of such concentrated streams. Furthermore, the use of cellulose acetate membranes in a lignocellulosic system may not be feasible since such membranes could be destroyed by cellulase enzymes.

A method for the processing of lignocellulosic feedstock to produce a sugar stream is required that addresses the problems associated with high inorganic salt concentrations. The development of such a method would represent a significant step forward in the commercialization of, for example, ethanol production from lignocellulosic biomass.

BRIEF SUMMARY OF THE INVENTION

The present invention relates to a method for processing lignocellulosic feedstocks. More specifically, the present invention provides a method for recovering inorganic salt during the processing of lignocellulosic feedstocks.

It is an object of the invention to provide a method for recovery of inorganic salt during processing of lignocellulosic feedstocks.

According to the present invention, there is provided a method (A) for processing a lignocellulosic feedstock and obtaining an inorganic salt, the method comprising:

a. pretreating the lignocellulosic feedstock by adding one or more than one soluble base to the lignocellulosic feedstock to produce a pretreated lignocellulosic feedstock;
b. adding one or more than one acid to the pretreated lignocellulosic feedstock to adjust the pH of the pretreated lignocellulosic feedstock produce a neutralized feedstock;
c. hydrolyzing the neutralized feedstock to produce a sugar stream and a hydrolyzed feedstock; and
d. recovering the inorganic salt from a stream obtained from the neutralized feedstock, the sugar stream, or a combination thereof.

Preferably, the inorganic salt is soluble.

The lignocellulosic feedstock used in the method as described above may be selected from the group consisting of corn stover, wheat straw, barley straw, canola straw, rice straw, oat straw, soybean stover, grass, switch grass, miscanthus, cord grass, and reed canary grass, aspen wood, sawdust, bagasse and beet pulp.

The present invention also pertains to the method (A) described above, wherein the inorganic salt comprises ammonium sulfate salts, ammonium phosphate salts, potassium phosphate salts, ammonium carbonate salts, ammonium chloride salts, ammonium sulfite salts, potassium sulfate salts, potassium chloride salts or a mixture thereof. Preferably, the salt comprises ammonium sulfate salts, ammonium phosphate salts, ammonium chloride salts, or a mixture thereof. Ammonium carbonate salts may be decomposed to form ammonia and carbon dioxide, followed by recovery of the ammonia.

The present invention also relates to the method (A) described above, wherein, in the step of recovering (step d.), the inorganic salt is recovered by ion exclusion. The step of recovering may be followed by crystallization of the inorganic salt, electrodialysis, drying, or agglomeration and granulation. Alternatively, the inorganic salt may be concentrated by evaporation, membrane filtration, or a combination thereof, prior to recovery to produce a concentrated solution comprising the inorganic salt. The concentrated solution may be clarified by membrane filtration, plate and frame filtration, or centrifugation prior to recovery.

Moreover, the present invention pertains to the method (A) described above, wherein the one or more than one soluble base is selected from the group consisting of ammonia, ammonium hydroxide, potassium hydroxide and sodium hydroxide. Preferably, the soluble base is ammonium hydroxide or ammonia. When ammonium hydroxide or ammonia is employed, the pretreatment may be performed at a temperature from about 20° C. to about 200° C., at a pH from about 9.5 to about 12 and/or for a time period of from about 2 to about 20 minutes.

Furthermore, the present invention relates to the method (A) described above, wherein the one or more than one acid is selected from the group consisting of sulfuric acid, sulfurous acid, sulfur dioxide, phosphoric acid, carbonic acid, carbon dioxide, hydrochloric acid and a combination thereof. Preferably, the acid is sulfuric acid.

The present invention also pertains to the method (A) as described above, wherein, in the step of hydrolyzing (step c.), one or more than one cellulose enzyme is added to the neutralized feedstock so that at least a portion of the cellulose in the neutralized feedstock is hydrolyzed to produce glucose. Alternatively, the step of hydrolyzing, the neutralized feedstock is treated with one or more than one acid so that at least a portion of cellulose and hemicellulose in the neutralized feedstock is hydrolyzed to produce a sugar stream comprising glucose, xylose, arabinose, mannose and galactose.

In addition, the present invention pertains to the method (A) as described above, wherein, after the step of hydrolyzing (step c.), the sugar stream is separated from the hydrolyzed feedstock to form a solid residue and a sugar hydrolyzate stream. The inorganic salt may then concentrated prior to recovery by evaporation, membrane filtration, or a combination thereof.

The present invention also relates to the method (A) as described above, wherein the inorganic salt is for use as a fertilizer. Inorganic salts suitable for use as a fertilizer include ammonium sulfate, ammonium phosphate, potassium phosphate, ammonium chloride, potassium sulfate, potassium chloride or a combination thereof.

Furthermore, the present invention pertains to the method (A) described above further comprising the steps of:
e. fermenting the sugar stream to produce a fermentation broth comprising ethanol; and
f. distilling the fermentation broth to produce concentrated ethanol and still bottoms.

Optionally, the inorganic salt is recovered from the still bottoms followed by purifying the inorganic salt. Prior to the step of recovering the inorganic salt from the still bottoms, the concentration of the still bottoms may be increased by evaporation, membrane filtration, or a combination thereof, to produce concentrated still bottoms, followed by a step of ion exclusion chromatography using a simulated moving bed (SMB) process. The concentrated still bottoms may be clarified by microfiltration, plate and frame filtration or centrifugation prior to the step of ion exclusion chromatography. The step of purifying the inorganic salt may comprise crystallization of the inorganic salt or electrodialysis, drying or agglomeration and granulation.

The present invention also pertains to a method (B) for processing of a lignocellulosic feedstock and obtaining an inorganic salt which comprises:
a. pretreating the lignocellulosic feedstock by adding one or more than soluble base to the lignocellulosic feedstock to produce a pretreated lignocellulosic feedstock;
b. adding one or more than one acid to the pretreated lignocellulosic feedstock to adjust the pH of the pretreated lignocellulosic feedstock to produce a neutralized feedstock;
c. hydrolyzing the neutralized feedstock to produce a sugar stream and a hydrolyzed feedstock;
d. fermenting the sugar stream to produce a fermentation broth comprising ethanol or butanol;
e. separating ethanol or butanol from the fermentation broth by distillation, membrane filtration, liquid-liquid extraction or gas stripping to produce concentrated ethanol or butanol and an aqueous stream comprising the inorganic salt; and
f. recovering the inorganic salt from the aqueous stream to produce a recovered inorganic salt.

The present invention also pertains to the method (B) described above further comprising the steps of purifying the recovered inorganic salt to obtain a purified inorganic salt and producing a product comprising the purified inorganic salt. The step of purifying may comprise performing ion exclusion chromatography, followed by electrodialysis, drying, agglomeration and granulation, or crystallization.

The present invention also provides a method (C) for processing a lignocellulosic feedstock and obtaining an inorganic salt, the method comprising:
a. pretreating the lignocellulosic feedstock by adding one or more than one soluble base comprising ammonia or ammonium hydroxide, or a combination thereof, to the lignocellulosic feedstock to produce a pretreated lignocellulosic feedstock;
b. adding one or more than one acid comprising sulfuric acid to the pretreated lignocellulosic feedstock to adjust the pH of pretreated lignocellulosic feedstock produce a neutralized feedstock and an inorganic salt comprising ammonium sulfate; and
c. recovering the inorganic salt from a stream obtained from the neutralized feedstock, the sugar stream, or a combination thereof.

Preferably, the ammonium sulfate is for use as a fertilizer.

The present invention also relates to the method (C) as described above, wherein the step of pretreating (step a.) is performed at a temperature from about 20° C. to about 200° C., at a pH from about pH 9.5 to about 12 and for a time period of from about 2 to about 20 minutes.

The present invention also relates to the method (C) as described above, wherein, in the step of recovering (step c.), the inorganic salt is recovered by ion exclusion. The step of recovering (step c.) may be followed by crystallization of the inorganic salt, electrodialysis, drying, or agglomeration and granulation.

The present invention also provides a method (D) for processing a lignocellulosic feedstock and obtaining an inorganic salt, the method comprising:
a. pretreating the lignocellulosic feedstock by adding one or more than one soluble base to produce a pretreated lignocellulosic feedstock;
b. washing the pretreated lignocellulosic feedstock to produce a wash stream and a washed feedstock;
c. neutralizing the wash stream by treatment with one or more than one acid to produce a neutralized wash stream comprising an inorganic salt; and
d. recovering a salt comprising the inorganic salt from the neutralized wash stream.

Preferably, the inorganic salt is for use as a fertilizer.

The present invention also pertains to the method (D) as defined above, wherein, in the step of recovering (step d.), the inorganic salt comprises ammonium sulfate salts, ammonium phosphate salts, potassium phosphate salts, ammonium carbonate salts, ammonium chloride salts, ammonium sulfite salts, potassium sulfate salts, potassium chloride salts, or a mixture thereof. Preferably, the salt comprises ammonium sulfate salts, ammonium phosphate, ammonium chloride salts, or a mixture thereof. The ammonium carbonate salts may be decomposed to form ammonia and carbon dioxide and the ammonia may then be recovered.

The present invention also pertains to the method (D) as described above, wherein, in the step of neutralizing (step c.), the one or more than one acid is selected from the group consisting of sulfuric acid, sulfurous acid, sulfur dioxide, phosphoric acid, carbonic acid, carbon dioxide, hydrochloric acid and a combination thereof.

Furthermore, the present invention pertains to the method (D) as defined above, wherein the wash stream is neutralized by treatment with a strong acid cation exchange resin.

The process of the present invention overcomes several disadvantages of the prior art by taking into account the difficulties in the conversion of lignocellulosic feedstocks to sugar and then ethanol. By removing inorganic salt during the processing of lignocellulosic feedstock, several of the steps operate more efficiently, for example enzymatic hydrolysis, or fermentation of sugar to ethanol, as the inhibitory effect of the salt is reduced. Furthermore, the inorganic salts recovered during this process and the value generated from these salts help offset the cost associated with the use of these salts. The present invention offers significant advances in the production of sugar, ethanol, and other products from lignocellulosic feedstocks.

This summary of the invention does not necessarily describe all features of the invention. These and other features of the invention will become more apparent from the following description in which reference is made to the appended drawings.

DETAILED DESCRIPTION OF THE INVENTION

Figure 1:
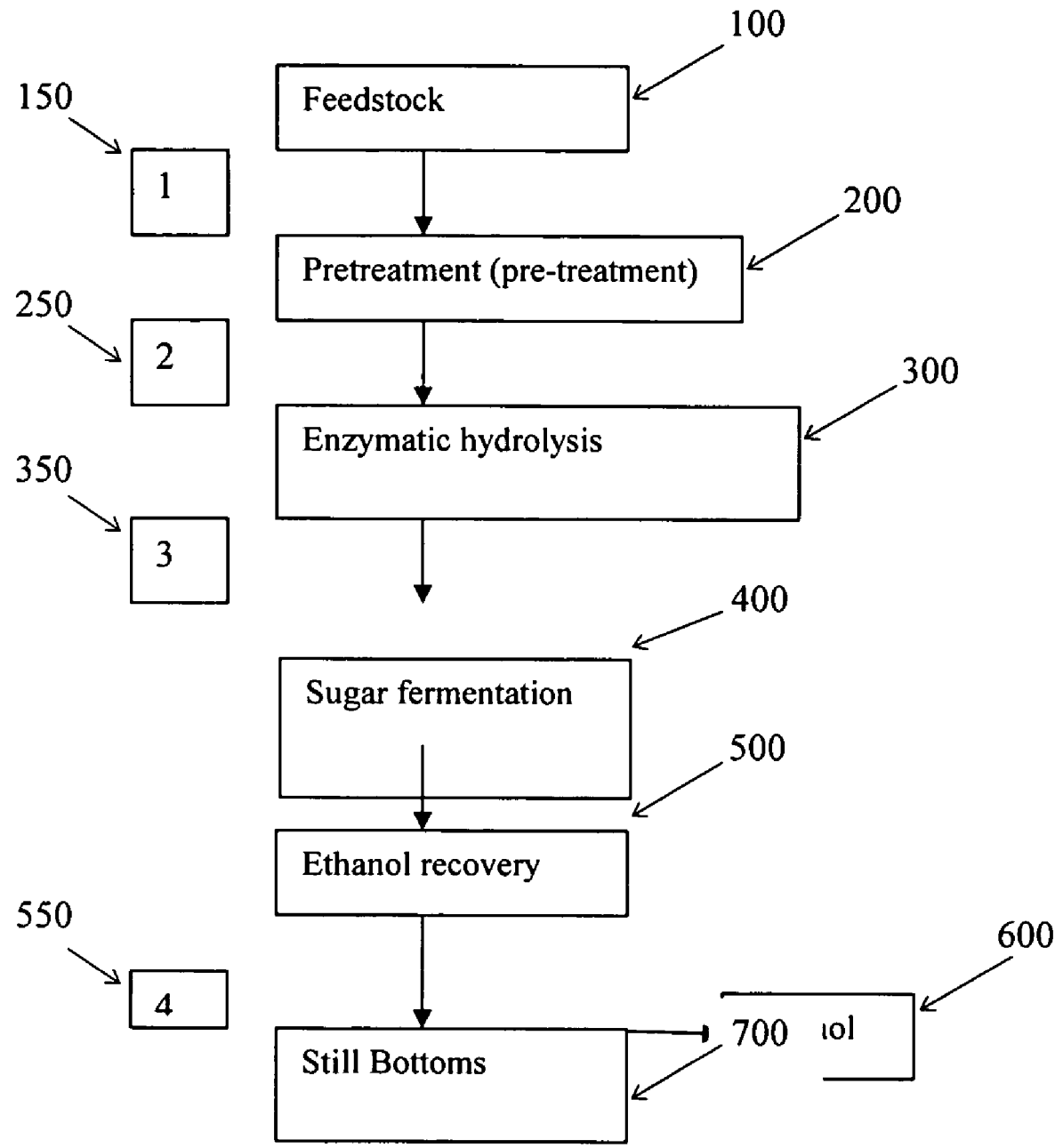
FIG. 1 shows a schematic outline of the process of the present invention, and indicates several stages where inorganic salt may be removed and recovered (indicated as stages 1-4).

The present invention relates to a method for processing lignocellulosic feedstocks. More specifically, the present invention provides a method for recovering inorganic salt during the processing of lignocellulosic feedstocks.

The following description is of a preferred embodiment.

The present invention provides a process for the recovery of inorganic salt during the conversion of a lignocellulosic feedstock to sugar. The inorganic salt may be used as fertilizer or for other purposes as desired.

The feedstock for the process is a lignocellulosic material. By the term "lignocellulosic feedstock", it is meant any type of plant biomass such as but not limited to non-woody plant biomass, cultivated crops such as, but not limited to grasses, for example but not limited to C4 grasses, such as switch grass, cord grass, rye grass, miscanthus, reed canary grass, or a combination thereof, or sugar processing residues such as baggase, or beet pulp, agricultural residues, for example, soybean stover, corn stover, rice straw, rice hulls, barley straw, corn cobs, wheat straw, canola straw, rice straw, oat straw, oat hulls, corn fiber, recycled wood pulp fiber, sawdust, hardwood, for example aspen wood and sawdust, softwood, or a combination thereof. Further, the lignocellulosic feedstock may comprise cellulosic waste material such as, but not limited to newsprint, cardboard, sawdust and the like. Lignocellulosic feedstock may comprise one species of fiber or alternatively, lignocellulosic feedstock may comprise a mixture of fibers that originate from different lignocellulosic feedstocks. Furthermore, the lignocellulosic feedstock may comprise fresh lignocellulosic feedstock, partially dried lignocellulosic feedstock, fully dried lignocellulosic feedstock or a combination thereof.

Lignocellulosic feedstocks comprise cellulose in an amount greater than about 20%, more preferably greater than about 30%, still more preferably greater than about 40% (w/w). The lignocellulosic feedstock also comprises lignin in an amount greater than about 10%, or, more typically, in an amount greater than about 15% (w/w). The lignocellulosic feedstock also comprises a combined amount of sucrose, fructose and starch in an amount less than about 20%, generally less than about 10% (w/w).

By the term "inorganic salt", it is meant salts that do not contain either a cation or an anion with carbon-hydrogen bonds. This term is meant to exclude salts containing acetate anions, oxalate anions and other organic anions. These salts, and other salts containing an anion with a carbon-hydrogen bond, are "organic salts".

Preferably, the inorganic salt is soluble. By the term "soluble inorganic salt", it is meant that the inorganic salt has a solubility in water that is at least 0.1 M at 20° C. Calcium hydroxide, lime and calcium sulfate are examples of insoluble inorganic salts.

The presence of inorganic salts within the processing of the lignocellulosic feedstock can lead to the degradation of xylose. Degradation of xylose results in reduced yields of sugar, ethanol or a combination thereof. Furthermore, the inorganic salt has an adverse impact on the enzymatic hydrolysis and yeast fermentation processes.

The processes described herein recover the inorganic salt from the product streams. The inorganic salts are recovered by, for example, ion exclusion, ion exchange or electrodialysis. The removal of salts produces a stream with greater xylose stability. Any inorganic salt, for example potassium sulfate or ammonium sulfate, that is recovered as a by-product during the processing of lignocellulosic feedstocks may be used for a variety of purposes, for example within a fertilizer. Moreover, since acid and alkali are costly, the recovery of inorganic salts resulting from the neutralization improves the economic viability of the process.

By the term "ion-exchange", it is meant a separation technique that employs a chemical reaction in which an ion from solution is exchanged for a similarly charged ion attached to an immobile solid particle. The ion exchange resins may be cation exchangers that have positively charged mobile ions available for exchange, or anion exchangers, whose exchangeable ions are negatively charged. The solid ion exchange particles may be either naturally occurring inorganic zeolites or synthetically produced organic resins.

By the term "ion exclusion", it is meant a separation technique that separates ionic species in solution from non-ionic species, or weakly ionic species from strongly ionic species, by employing a resin having a structure that allows the non-ionic species or weakly ionic species to diffuse into it while preventing more ionic species from entering the resin. The species with less ionic character then elutes after the more ionic species.

As used herein, the term "membrane filtration" refers to any process of filtering a solution with a membrane that is suitable for concentrating a solution. Included in this definition are microfiltration, which employs membranes of a pore size of 0.05-1 microns for the removal of particulate matter; ultrafiltration, which employs membranes with a cut-off of 500-50,000 mw for removing large soluble molecules; and reverse osmosis using nanofiltration membranes to separate small molecules from water. The term "reverse osmosis" refers to the separation of solutions having different solute concentrations with a semi-permeable membrane by applying sufficient pressure to the more concentrated liquid to reverse the direction of osmosis across the membrane. The term "nanofiltration" refers to processes that separate solutions of differing solute concentrations using reverse osmosis, but that employ membranes which generally have a larger pore size than those used in reverse osmosis. For the purposes of this specification, the term "membrane filtration" also encompasses "pervaporation". Pervaporation refers to a method for the separation of mixtures of liquids by partial vaporization through a membrane.

In addition to concentrating a solution, microfiltration may be used for clarification.

Separation by ion exclusion may employ Simulated Moving Bed (SMB) technology. As used herein, the term "Simulated Moving Bed" or "SMB" refers to an ion exclusion chromatographic separation process that utilizes a set of columns interconnected in series in which liquid circulates in the unit by simultaneous shifting of the columns in the opposite direction. As used herein, this term encompasses Improved Simulated Moving Bed (ISMB) systems. A non-limiting example of an ISMB system is provided in Example 1. SMB is a preferred separation method for ion exclusion chromatography since solvent use is minimized, thereby leading to a greatly reduced cost of operation when compared to traditional batch chromatography methods.

Prior to separation by ion exclusion, the inorganic salt solution may be concentrated and clarified. Concentration may be carried out by evaporation or by microfiltration (0.14 microns) to remove particles, ultrafiltration (500-2000 mw cut off) to remove soluble lignin and other large molecules and reverse osmosis to increase solids to a concentration of about 12 to about 20%, or any amount therebetween, followed by evaporation. Following concentration, the solution may be clarified by microfiltration, plate and frame filtration or centrifugation.

After separation from the product stream, the inorganic salt may be crystallized, dried or subjected to electrodialysis or agglomeration and granulation, and used as desired, for example, as a solid fertilizer. Alternatively, the inorganic salt may be concentrated as a wet slurry and used in a liquid form, for example as a liquid fertilizer. The remaining components within the product streams, for example sugar, may be further processed or collected, as desired.

By the term "electrodialysis", it is meant a separation process in which ions are transported across a semi-permeable membrane under the influence of an electric potential. The membrane may be either cation or anion selective to allow for the separation of cations or anions, respectively.

By the term "crystallization", it is meant any process for the formation of solid particles or crystals of a solute from a saturated solution. This can be carried out by concentration, cooling (under vacuum or with a heat exchanger), reaction displacement or equilibrium displacement.

By the term "agglomeration and granulation", it is meant process steps to modify particle size, for example, to improve bulk properties. Non-limiting examples of bulk properties that can be improved include, but are not limited to, dissolving behavior, form and stability of the granulated product and storage stability.

By the term "drying", it is meant any process for removing water, volatile components or other liquids from a solid material, to reduce the content of residual liquid to an acceptable low value. This includes, but is not limited to, direct and indirect drying. Direct drying refers to using direct contact of hot gases to drive off some, or all of the water, and indirect drying refers to contact with a heated surface as opposed to hot gas.

The inorganic salts in the product stream result from the lignocellulosic feedstock itself, and from the acids and bases used during the processing of the lignocellulosic feedstock. For example, the inorganic salt mixtures that arise from sulfuric acid include mixtures of sulfuric acid, sodium bisulfate, and disodium sulfate, depending on the pH of the system and on the total ionic concentration. For this discussion, these salt mixtures will be referred to as "sodium sulfate salts". Other salt mixtures may also be present in the product streams for example, but not limited to, ammonium sulfate salts (sulfuric acid, ammonium bisulfate, and diammonium sulfate); sodium sulfite salts, (sulfurous acid, sodium bisulfite, and disodium sulfite); ammonium sulfite salts (sulfuric acid, ammonium bisulfite, and diammonium sulfite), sodium phosphate salts (phosphoric acid, sodium dihydrogen phosphate, and disodium hydrogen phosphate), ammonium phosphate salts (phosphoric acid, diammonium hydrogen phosphate, and ammonium dihydrogen phosphate), potassium sulfate salts (sulfuric acid, potassium bisulfate, and dipotassium sulfate), potassium sulfite salts (sulfuric acid, potassium bisulfite, and dipotassium sulfite), and potassium phosphate salts (phosphoric acid, potassium dihydrogen phosphate, and dipotassium hydrogen phosphate).

The inorganic salts recovered from the process as described herein have value as a fertilizer; however, additional uses of the recovered salts may be exploited as desired. In the case of fertilizer, ammonium, potassium, sulfate, and phosphate salts are typically of value. Other compounds present, including inorganic salts of sodium and sulfite salts, may be of less value in fertilizer. However, these inorganic salts can be converted to forms of higher value. For example, which is not to be considered limiting, sodium salts can be converted to potassium salts by the use of ion exchange. In this example, sodium hydroxide may be used for some or all of the neutralization of sulfuric acid during the processing of a lignocellulosic feedstock and the sodium ion exchanged with potassium using a cation exchange resin. The resulting potassium salt may then be of more value as a fertilizer.

Additionally, sulfite salts can be converted to sulfate salts by oxidation with air or with oxidizing agents. For example, sulfurous acid or sulfur dioxide present in pretreatment may be used to oxidize the sulfite salts to sulfate for use in fertilizer.

The step of pretreatment increases the susceptibility of the lignocellulosic feedstock to hydrolysis by cellulase enzymes. In the case of acid pretreatment, hemicellulose, or a portion thereof, that is present in the lignocellulosic feedstock is hydrolyzed to monomeric sugars, for example xylose, arabinose, mannose, galactose, or a combination thereof. Preferably, the acid pretreatment is designed to carry out almost complete hydrolysis of the hemicellulose and a small amount of conversion of cellulose to glucose. The cellulose is hydrolyzed to glucose in a subsequent step that uses cellulase enzymes. Typically a dilute acid, from about 0.02% (w/v) to about 1% (w/v), or any amount therebetween, is used for the acidic pretreatment of the lignocellulosic feedstock. The preferred acid for pretreatment is sulfuric acid. Acid pretreatment is familiar to those skilled in the art, see for example U.S. Pat. No. 5,536,325 (Brink); U.S. Pat. No. 4,237,226 (Grethlein; which are incorporated herein by reference). Other methods that are known within the art may be used as required for preparation of a pretreated feedstock, for example, but not limited to, those disclosed in U.S. Pat. No. 4,556,430 (Converse; which are incorporated herein by reference).

Preferably, the step of reacting the acidified feedstock is performed at a temperature between about 100° C. to about 280° C., or any amount therebetween, for example a temperature of 100, 120, 140, 160, 180, 200, 22, 0, 240, 260, 280° C., or any amount therebetween, at a pH from about pH 0.4 to about pH 2.5 or any amount therebetween, for example, a pH of 0.4, 0.6, 0.8, 1.0, 1.2, 1.4, 1.6, 1.8, 2.0, 2.2, 2.4, 2.5, or any amount therebetween, for about 5 seconds to about 60 minutes, or any amount therebetween, for example, for 5, 10, 20, 30, 40, 50 60 seconds, or for 1.5, 2, 4, 6, 8, 10, 15, 20, 25, 30, 35, 40, 45, 50, 55, 60 minutes, and any amount therebetween. It is understood by those skilled in the art that the feedstock temperature is that of the feedstock itself, which might differ from the temperature measured outside the reaction chamber. Devices used to carry out this pretreatment include, but are not limited to sealed batch reactors, continuous extruders and steam guns.

An example of a suitable acidic pretreatment, without intending to be limiting, is steam explosion described in U.S. Pat. No. 4,416,648 (Foody; which is incorporated herein by reference). A typical set of pretreatment conditions for processing lignocellulosic feedstocks is a temperature of about 170° C. to about 260° C., for a period of about 0.1 to about 30 minutes and/or at a pH of about 0.4 to about 2.0.

It is also within the scope of the present invention that a two-stage acid pretreatment process may be used, whereby the first stage improves the cellulose hydrolysis somewhat while solubilizing primarily the hemicellulose but little cellulose. The second stage then completes a full pretreatment. Using this method, the first stage reaction is run at a temperature of less than about 180° C. while the second stage reaction is run at a temperature of greater than about 180° C. Preferably, the first stage of the reaction is carried out at a temperature of about 60° C. to about 140° C., or an amount therebetween, for 0.25 to 24 hours, or any amount therebetween, and at a pH from about pH 0.5 to about pH 2.5, or any amount therebetween. More preferably, the first stage of pretreatment is carried out at a temperature of 100° C. to 130° C. for 0.5 to 3 hours at pH 0.5 to 2.5. While the second stage of reaction may be carried out at a temperature of 180° C. to 270° C., at pH 0.5 to 2.5 for a period of 5 seconds to 120 seconds. The two-stage pretreatment provides separate recovery of the soluble monomers from hemicellulose for downstream processing.

Furthermore, the lignocellulosic feedstock may be processed using the methods disclosed in WO 02/070753 (Griffin et al., which is incorporated herein by reference). A pretreatment process using flow-through hydrolysis is disclosed in U.S. Pat. No. 4,237,226 (Grethlein et al., which is incorporated herein by reference).

Any acid can be used to adjust the pH of the lignocellulosic feedstock during acid pretreatment. However, preferred acids are sulfuric acid, sulfurous acid, sulfur dioxide, and phosphoric acid, due to their low cost, effectiveness in pretreatment, and, in the case of sulfate and phosphate salts, their further use within a fertilizer. A suitable alternative to sulfuric acid is phosphoric acid.

Alternatively, the pretreatment involves the addition of alkali to produce an alkali pretreated feedstock. Without wishing to be bound by theory, alkali pretreatment typically does not hydrolyze hemicellulose, but rather the base reacts with acidic groups present on the hemicellulose to open up the surface of the substrate. In addition, the base may alter the crystal structure of the cellulose so that it is more amenable to hydrolysis.

Bases that may be used in the pretreatment include ammonia, ammonium hydroxide, potassium hydroxide, and sodium hydroxide. The base used in the pretreatment is preferably soluble in water, which excludes lime or magnesium hydroxide. Lime pretreatment is subject to the disadvantages described previously.

An example of a suitable alkali pretreatment is Ammonia Freeze Explosion, or Ammonia Fiber Explosion ("AFEX" process). According to this process, the lignocellulosic feedstock is contacted with ammonia or ammonium hydroxide in a pressure vessel. The contact is maintained for a sufficient time to enable the ammonia or ammonium hydroxide to swell (i.e., decrystallize) the cellulose fibers. The pressure is then rapidly reduced which allows the ammonia to flash or boil and explode the cellulose fiber structure. (See U.S. Pat. Nos. 5,171,592, 5,037,663, 4,600,590, 6,106,888, 4,356,196, 5,939,544, 6,176,176, 5,037,663 and 5,171,592 which are incorporated herein by reference.) The flashed ammonia may then be recovered according to known processes. However, this only removes a portion of the ammonia and any remaining ammonia may be neutralized with acid to produce an inorganic salt. The inorganic salt, in turn, is recovered using the processes described herein. Alternatively, the ammonia is not recovered by flashing, in which case, all or a portion of the ammonia is neutralized with acid.

The step of reacting the feedstock with ammonia or ammonium hydroxide may be performed at a temperature between about 20° C. to about 200° C., or any temperature therebetween. For example, the temperature may be 20, 40, 60, 80, 100, 120, 140, 160, 180, or 200° C. The pH is typically from about pH 9.5 to about pH 12, or any pH therebetween. For example, the pH of the feedstock may be 9.5, 9.8, 10.0, 10.2, 10.4, 10.6, 10.8, 11.0, 11.2, 11.4, 11.6, 11.8 or 12.0. The treatment time may be from 2 minutes to about 20 minutes, or any amount of time therebetween. For example, the duration of the pretreatment may be 2, 3, 4, 5, 6, 7, 8, 9, 10, 11, 12, 13, 14, 15, 16, 17, 18, 19 or 20 minutes. The moisture content of the feedstock may be between 50% and 70%, or any range therebetween; for example, the moisture content may be 50, 52, 54, 56, 58, 60, 62, 64, 66, 68 or 70%. The ammonia or ammonium hydroxide is added to achieve a concentration which is generally about 0.5 to about 2.5 times the mass of the feedstock on a dry basis, or any amount therebetween. For example, the ammonia concentration may be about 0.5, 0.7, 0.8, 0.9, 1.0, 1.2, 1.4, 1.6, 1.8, 2.0, 2.2, 2.4 or 2.5 times the mass of the feedstock on a dry basis.

If the feedstock is pretreated with sodium hydroxide or potassium hydroxide, the temperature may be between about 120° C. to about 220° C., or any temperature range therebetween. For example, the temperature may be 120, 130, 140, 150, 160, 170, 180, 190, 200, 210 or 220° C. The pH is typically between about 10 to about 13, or any pH range therebetween. For example, the pH may be 10.0, 10.5, 11.0, 11.5, 12.0, 12.5 or 13.0. The treatment time may be from about 15 minutes to about 120 minutes, or any range therebetween. The treatment time may be 15, 20, 30, 40, 50, 60, 70, 80, 90, 100, 110 or 120 minutes.

The pretreated feedstock may be washed to remove the sugar-acid mixture or sugar-base mixture, depending on the pretreatment, from the solids portion. The separated acid stream or alkaline stream may then be neutralized and inorganic salt recovered from this stream. After salt removal from the neutralized wash stream, the feedstock solids remaining may be neutralized and processed for sugar fermentation or enzymatic or acid hydrolysis, as described below. The inorganic salt recovered from the wash stream obtained from the pretreated lignocellulosic feedstock may be concentrated, or dried as described herein.

The pretreated lignocellulosic feedstock is highly acidic or alkali, depending on the chemical used in pretreatment. It is neutralized prior to enzymatic hydrolysis and sugar fermentation. Cellulase enzymes are active over a range of pH of about 3 to about 7, or any range therebetween, preferably, the pH is from about 4.0 to about 6.0, or any range therebetween, and more preferably the pH is from about 4.5 to about 5.0, or any range therebetween. For example, the pH is 3.0, 3.5, 3.7, 4.0, 4.2, 4.5, 4.7, 5.0, 5.2, 5.5, 6.0, 6.5, 7.0, or any amount therebetween. Yeast and *Zymomonas* bacteria are typically used for sugar fermentation. The optimum pH for yeast is from about pH 4 to about pH 5, while the optimum pH for *Zymomonas* is from about pH 5 to about pH 6.

In principle, any soluble base can be used to adjust the pH of acidic material. However, it is preferred that the base used for pH adjustment of acid material is ammonia gas or ammonia dissolved in water for example, ammonium hydroxide. Sodium hydroxide or potassium hydroxide may also be used. These compounds are inexpensive, effective, and, in the case of ammonium and potassium salts, of high value if the inorganic salt is to be used in fertilizer.

By the term "soluble base", it is meant a base that has a solubility in water that is at least 0.1 M at 20° C. This term is meant to exclude salts that are slightly soluble or insoluble. Examples of bases that are excluded are $CaCO_3$ and $Ca(OH)_2$. Insoluble bases cannot be recovered according to the methods of the present invention. The term "base" is meant to encompass any species that, when dissolved in water, gives a solution with a pH that is more than 7.

If an alkaline pretreatment is carried out, an acid is used to neutralize the pretreated feedstock. Non-limiting examples of acids that may be used in the neutralization step are sulfuric acid, sulfurous acid, sulfur dioxide, phosphoric acid, carbonic acid, carbon dioxide, hydrochloric acid, or a combination thereof. In the case of a pretreatment carried out with ammonia or ammonium hydroxide, the pH may be adjusted with sulfuric acid, phosphoric acid, hydrochloric acid, carbon dioxide/carbonic acid or sulfurous acid which produces the inorganic salts ammonium sulfate, ammonium phosphate, ammonium chloride, ammonium carbonate or ammonium sulfite, respectively. If potassium hydroxide is used in the pretreatment, the feedstock may be neutralized with phosphoric acid to produce potassium phosphate. These inorganic salts may be used directly as a fertilizer or, in the case of ammonium sulfate or ammonium carbonate, subjected to degradation reactions to produce ammonia, which, in turn, may be recovered and/or recycled in the process.

For example, ammonium carbonate may be decomposed to produce ammonia and carbon dioxide. The decomposition may involve thermal treatment to liberate the ammonia and carbon dioxide. The ammonia and/or the carbon dioxide may then be recovered, for example by distillation, stripping or evaporation. The recovered ammonia may, in turn, be recycled to the alkaline pretreatment step.

Preferably, the alkali pretreatment comprises addition of ammonia or ammonium hydroxide, followed by neutralization with sulfuric acid to produce ammonium sulfate. It will be understood by those of skill in the art that the ammonia may be provided in anhydrous form. The ammonium sulfate produced during the neutralization may be used directly as a fertilizer, or, alternatively, may be subjected to thermal decomposition according to the method of a co-pending U.S. application entitled "Process for Producing Ammonia and Sulfuric Acid from a Stream Comprising Ammonium Sulfate" (Curren et al.) to produce sulfuric acid and sulfate salts, such as ammonium sulfate.

As described previously, after alkali pretreatment, the aqueous phase may be separated from the pretreated feedstock solids to produce a wash stream. Neutralization may be carried out by direct addition of acid to the alkaline wash stream or may involve treatment of the wash stream with a strong acid cation exchange resin. This may involve passage of the wash stream through a column packed with a sulfonated polystyrene resin cross-linked with divinyl benzenes in an alkali/alkaline earth metal form. After neutralization, recovery of the inorganic salt from the neutralized wash stream may be carried out using the methods described herein.

Following neutralization of the pretreated lignocellulosic feedstock by the addition of the soluble base or the acid, depending on the pretreatment, enzymatic hydrolysis may be carried out. Typically, the enzymes used for hydrolysis are cellulase enzymes that hydrolyze the cellulose to glucose. Any cellulase may be used; however, preferred cellulase enzymes are those made by the fungus *Trichoderma*. Preferably, the enzyme treatment is carried out between about 40° C. to about 60° C., or any temperature range therebetween, or between about 45° C. and about 55° C., or any temperature range therebetween. For example, the enzyme treatment may be carried out at 40, 42, 44, 46, 48, 50, 52, 54, 56, 58, 60° C., or any amount therebetween. The treatment may be performed for a time period of about 1 to about 10 days, or any time interval therebetween, or for a time period of about 3 to about 7 days, or any time interval therebetween. For example, the treatment may be performed for a time period of 1, 2, 3, 4, 5, 6, 7, 8, 9 or 10 days, or any time period therebetween.

Following enzymatic hydrolysis, the aqueous phase containing the sugar, inorganic salts, and other soluble compounds may be separated from the insoluble, un-hydrolyzed solids phase to produce a soluble sugar stream (also referred to as the wash stream). The un-hydrolyzed solids are primarily lignin and cellulose, and, to a lesser extent, silica, insoluble salts and other compounds. The sugar stream can be pumped, mixed, and controlled more easily than a slurry containing liquids and insoluble solids. The insoluble solids are separated from the sugar stream by any suitable method, for example but not limited to plate and frame filtration, crossflow filtration, centrifugation, or other methods known to one of skill in the art.

As an alternative to enzyme hydrolysis, the pretreated feedstock may be subjected to acid hydrolysis. This may involve hydrolyzing the pretreated feedstock with steam and sulfuric acid at a temperature, acid concentration, and length of time that are sufficient to hydrolyze the cellulose to glucose and hemicellulose to xylose and arabinose. The sulfuric acid can be concentrated (25-90% w/w) or dilute (3-8% w/w).

Sugars present in the sugar stream, for example glucose, xylose, arabinose, mannose, galactose, or mixtures thereof, may be fermented by microbes. The fermentation products can include any desired products that generate value to the fermentation plant. The preferred fermentation products are ethanol, butanol or lactic acid, which have large markets and are made efficiently by many microbes. For ethanol production, fermentation can be carried out by one or more than one microbe that is able to ferment the sugars to ethanol. For example, the fermentation may be carried out by recombinant *Saccharomyces* yeast that has been engineered to ferment glucose, mannose, galactose and xylose to ethanol, or glucose, mannose, galactose, xylose, and arabinose to ethanol. Recombinant yeasts that can ferment xylose to ethanol are described in U.S. Pat. No. 5,789,210 (the contents of which are herein incorporated by reference). The yeast produces a fermentation broth comprising ethanol in an aqueous solution. For lactic acid production, the fermentation can be carried out by one or more than one microbe that ferments the sugars to lactic acid. Butanol production may involve the addition of one or more than one microbe to a sugar stream to convert sugars to butanol. An example of a suitable microbe for fermenting sugars to butanol is *Clostridium acetobutylicum*.

If ethanol or butanol is the product, the alcohol may then be recovered from the fermentation broth. For example, the ethanol may be recovered by distillation of the fermentation broth. After recovery of the ethanol, for example by distillation, further ethanol purification may be carried out by adsorption or other methods familiar to one of skill in the art. The aqueous stream after distillation is still and contains yeast cells, inorganic salts, unfermented sugars, organic salts and other impurities. Butanol is preferably recovered from the fermentation broth by membrane filtration, liquid-liquid extraction or gas stripping to produce concentrated butanol.

Inorganic salts present in the still bottoms may also be recovered using any suitable method known to one of skill in the art, for example, but not limited to ion exclusion. These processes can be followed by crystallization, electrodialysis, drying, or agglomeration and granulation. A preferred method for recovering the inorganic salt from the still bottoms is increasing the concentration of the still bottoms by evaporation, membrane filtration, or a combination thereof, followed by clarification by microfiltration, plate and frame filtration and centrifugation. This is followed by ion exclusion chromatography using a simulated moving bed (SMB) process and then crystallization, electrodialysis, drying, or agglomeration and granulation.

Inorganic salts may also be removed from the lignocellulosic feedstock prior to pretreatment by washing, leaching, or a combination thereof to produce a liquid stream or "leachate". An example of a leaching process is described in WO 02/070753 (Griffin et al., which is incorporated herein by reference). This process involves contacting the lignocellulosic feedstock with water for two minutes or longer, and then separating the solids from the aqueous phase. This decreases the acid requirement for pretreatment, and decreases costs, and degradation of xylose, in the pretreatment process.

After leaching, the aqueous solution containing salts (the "leachate") contains potassium and other salts and trace elements that may be of value for subsequent use, for example within a fertilizer. The leachate may be concentrated by evaporation or filtered through a reverse osmosis membrane to remove the water or subjected to reverse osmosis and evaporation. The leachate may be subsequently clarified by microfiltration, plate and frame filtration or centrifugation. Leachate salts can be separated from organics by ion exclusion chromatography using a simulated moving bed (SMB) process to produce a product that is useable as a fertilizer. Either the liquid or the solid salt streams obtained from the leachate can be combined with other salt streams produced as described herein.

With reference to FIG. 1, there is shown an outline of an embodiment of the method of the present invention for the processing of lignocellulosic feedstock (100) to sugar (300, 400) and ethanol (600), through the successive processes of pretreatment (200), enzymatic hydrolysis (300), sugar fermentation (400), and ethanol recovery (500). As indicated in this figure, there are several steps leading to the production of ethanol where inorganic salt may be removed. For example, which is not to be considered limiting, inorganic salt may be removed at the stages indicated as 1, 2, 3, and 4 (150, 250, 350 and 550, respectively) in FIG. 1.

Following pretreatment with acid (200; FIG. 1), the lignocellulosic feedstock may be washed with water (250) to remove the inorganic salts at step 1. Prior to pretreatment, the acid, for example sulfuric acid, sulfurous acid, sulfur dioxide, or phosphoric acid, is added to the lignocellulosic feedstock to adjust the pH, for example, to about 0.4 to about 2.0, as described above. After pretreatment (200), the lignocellulosic feedstock is neutralized to a pH, for example, of about 4 to about 6 for example using ammonia or other alkali, as described above. The resulting inorganic salt can then be removed from the lignocellulosic feedstock at step 2 (250). The separation is carried out optionally by adding water to the pretreated lignocellulosic feedstock (200) and then separating the aqueous phase from the solids using a filter press, centrifuge or other suitable equipment. The aqueous stream (soluble stream) at this point is known as the pentose washings. The solids concentration in the pentose washings can be increased by evaporation, membrane filtration or a combination thereof.

The pentose washings containing ammonium sulfate and other inorganic salts can not be crystallized without further processing to remove the organic impurities. Ion exclusion by SMB chromatography can be used to separate the inorganic salts from the organic impurities. The inorganic salts can then be purified by crystallization or electrodialysis, drying, or agglomeration and granulation. The salt stream can then be used as a liquid fertilizer, or alternately dried and used as a solid fertilizer.

The resulting salt stream obtained following pretreatment of the lignocellulosic feedstock, either comprising sugars, or following removal of sugars, can be sold separately or combined with other salt streams obtained in the process described herein. For example, either the liquid or the solid salt streams obtained from the pentose washings can be combined with the salts from the leachate, indicated as step 1 in FIG. 1 (150), described above.

Preferably, the desalted sugar streams (pentose washings) are fermented to ethanol, since the desalted streams are easier to ferment than the streams containing salt.

The present invention also contemplates separating the aqueous salt and sugar stream from the un-hydrolyzed, insoluble solids following the enzymatic hydrolysis (300) at step 3 (350). The process for recovery of inorganic salts following enzymatic hydrolysis (300) at step 3 (350) is analogous to the process of salt recovery described above for pretreatment (200), at step 1 (150). For example, the wash stream obtained at step 3 (350) may be concentrated, or the sugars present in the wash stream obtained at step 3 removed and the remaining salt stream concentrated, and the sugar stream collected, or further processed at 400 (sugar fermentation) to produce ethanol.

The hydrolyzate stream produced following enzymatic hydrolysis (300), and containing salt and sugars is sent to fermentation (400), where yeast or other suitable microbes ferment the sugar to ethanol (600) or other products. If ethanol is made, it is recovered by distillation or other suitable means (500). The remaining slurry is the still bottoms (700) and contains unfermented sugars, inorganic salts, organic salts, yeast cells, and other compounds. The inorganic salts can be recovered from the still bottoms by means described above, and then used as desired, for example as a fertilizer.

Also shown in FIG. 1, is the removal of inorganic salts from the lignocellulosic feedstock prior to pretreatment (100) at step 1 (150). This may be carried out by leaching or other process, as described above.

An alkaline pretreatment followed by recovery of salt may be carried out as follows. This as an example of how the present invention can be practiced, and is not meant to be limiting in any manner.

Wheat straw is received in bales and chopped into pieces of size 20 mesh and smaller. The chopped straw is slurried in water to reach a moisture content of 70%. The wet straw is added to a reactor with pressurized ammonia slurry heated to 120° C. to reach a pressure of 300 psia. The mass of ammonia equal the mass of straw on a dry basis. The temperature is maintained for 20 minutes, after which the pressure is released quickly, which flashes off about 99% of the ammonia. The flash cools the reactor contents down to ambient temperature. The slurry is then adjusted to about pH 5.0 with concentrated sulfuric acid.

Upon acid addition, the soluble salt of ammonium sulfate is formed. The insoluble salt, calcium sulfate, is also formed.

The neutralized, cooled pretreated slurry is then added to a hydrolysis reactor and the reactor is mixed. The slurry consists of 4.5% undissolved solids, and the undissolved solids consist of 35% cellulose. Once the pretreated slurry is added to the hydrolysis reactor, cellulase and hemicellulase enzyme from *Trichoderma reesei* are added. The enzyme dosage is 35 mg protein per gram cellulose, which corresponded to a cellulase activity of 35.6 Filter Paper Units (FPU) per gram of cellulose and a xylanase activity of 275 xylanase units per gram of solids.

The hydrolysis runs for 2 days, at which point over 90% of the cellulose is converted to glucose and over 90% of the xylan is converted to xylose. The final glucose concentration is 6.0 to 8.0 g/L, with an average of 7.5 g/L. The hydrolysis slurry is filtered by using a vacuum filter to separate the unhydrolyzed solid residue from the aqueous stream. The unhydrolyzed solid residue contains primarily lignin, unhydrolyzed cellulose and silica, but also the insoluble salts such as calcium sulfate. The filtrate is essentially free of insoluble particles and contains glucose, xylose, and arabinose sugar; the soluble salts ammonium sulfate, potassium sulfate, magnesium sulfate and a small amount of dissolved calcium sulfate, and acetic acid, soluble lignin, and other dissolved organics.

The process stream is evaporated to increase the solids concentration ten-fold. The glucose concentration in the evaporated stream is 62 g/L, the xylose is 20 g/L, and the acetic acid is 2.0 g/L.

The evaporated stream is added to a fermentor to carry out sugar fermentation with yeast. The yeast strain is LNHST from Purdue University and has been genetically modified to enable it to ferment xylose, as well as glucose to ethanol. The strain is grown by propagation as described in U.S. Pat. No. 5,789,210. The fermentation is fed over a period of 7 hours and then run as a batch for 48 hours.

At the conclusion of the fermentation, the yeast cells are removed by centrifugation. The dilute beer is distilled to recover the ethanol from the aqueous solution, leaving still bottoms behind.

The ammonium sulfate salt is recovered from the still bottoms by evaporating the water to concentrate the salt and then crystallizing the salt.

The present invention may be illustrated in the following examples. However, it is to be understood that these examples are for illustrative purposes only, and should not be used to limit the scope of the present invention in any manner.

EXAMPLES

Example 1

Recovery of Soluble Inorganic Salt from a Hydrolyzate Sugar Stream

A sugar hydrolyzate stream containing sodium sulfate and other soluble inorganic salts was prepared as follows.

Feedstock Preparation

Wheat straw was received in bales measuring 3 feet by 3 feet by 4 feet. The wheat straw consisted of 60.3% carbohydrates, 18.7% lignin, 3.6% protein, 3.1% silica, and 4.9% non-silica inorganic salts. The inorganic salts included the cationic salt ions potassium (1.2%), calcium (0.57%), sodium (0.04%) and magnesium (0.15%), and the anionic ions chloride (0.22%) and phosphate (0.04%). The organic salt oxalate was also present at a concentration of 0.51%.

Two batches of 15 tonnes of the straw were hammer-milled to an average size of 1/8" and slurried in water at a ratio of 10 parts water to 1 part solids. The slurry was pumped through piping heated by direct injection with 350 psig steam to reach a temperature of 185° C. Once at this temperature, 10% sulfuric acid was added to reach a level of 0.9% acid on solids (w/w). The heated, acidified stock was held at this condition for 2 minutes as it passed through a pipe of 8 inches diameter.

Upon exiting the pipe, the slurry was flashed through a series of three cyclones to drop the temperature to 70° C. and adjusted to pH 5.0 with 30% concentrated sodium hydroxide. The slurry was finally cooled to 50° C. by passing it through a heat exchanger cooled with cold water.

Upon acid addition, the soluble inorganic salts of potassium sulfate, sodium sulfate, and magnesium sulfate were formed. The insoluble salt, calcium sulfate, was also formed. Upon neutralization with sodium hydroxide, which is soluble, the concentration of sodium sulfate in the slurry increased markedly. The calcium sulfate concentration was above the solubility limit and a portion of it precipitated and deposited on the cyclones and related piping. A portion of the organic salt calcium oxalate also deposited on the equipment.

Hydrolysis

The neutralized, cooled pretreated slurry was then pumped into three hydrolysis tanks, each of working volume of about 130,000 liters. The tanks are equipped with bottom-mounted eductors to mix the slurry; one of the three tanks has two side-mounted agitators. The slurry consisted of 4.5% undissolved solids, and the undissolved solids consisted of 55% cellulose. Once the hydrolysis tanks were filled or the pretreated slurry was exhausted, cellulase enzyme from *Trichoderma reesei* was added. The enzyme dosage was 25 mg protein per gram cellulose, which corresponded to a cellulase activity of 25.4 Filter Paper Units (FPU) per gram of cellulose.

The hydrolyses ran for 5 days, at which point over 90% of the cellulose was converted to glucose. The final glucose concentration was 26.0 to 28.0 g/L, with an average of 27.5 g/L. The hydrolysis slurries were pumped to a Lasta plate and frame filter press to separate the un-hydrolyzed solid residue from the aqueous stream. A polymeric flocculent was added in line at a level of 1-3 kg polymer/t solids to improve the rate of filtration. The filter cake was 45% solids. The un-hydrolyzed solid residue contains primarily lignin and un-hydrolyzed cellulose, but also the insoluble salts such as calcium sulfate. The aqueous process stream is essentially free of insoluble particles and contains glucose, xylose, and arabinose sugar; the soluble salts sodium sulfate, potassium sulfate, magnesium sulfate, and a small amount of dissolved calcium sulfate; and acetic acid and other dissolved organics.

The process stream was evaporated under vacuum using a four-effect evaporator at 90° C., 80° C., 70° C. and 45° C., respectively, to a volume of 81,700 liters with a solids concentration of 34%. Some of the acetic acid evaporated with the water, and some solids precipitated upon evaporation. The pH of the evaporated slurry was adjusted to pH 6.5 with 50% sodium hydroxide solution, and this caused more precipitation. The concentrated, pH-adjusted stream was sent to the Lasta plate and frame filter press a second time, with a Perlite filter aid, to remove the precipitated solids. The clear, evaporated process stream had inorganic salt concentrations of 105 g/L sodium sulfate, 40 g/L potassium sulfate, and 5 g/L magnesium sulfate. In addition, organic compounds present included 153 g/L glucose, 49 g/L xylose, 7.3 g/L arabinose, 3.4 g/L furfural, 3.5 g/L hydroxymethyl furfural, and 9.1 g/L acetate salt, an organic salt that was measured as acetic acid, and various trace metals (including trace quantities of calcium), and a significant amount of unidentified impurities.

Ion Exclusion Chromatography

The inorganic, soluble salts sodium sulfate, potassium sulfate, and magnesium sulfate were recovered from the concentrated process stream by ion exclusion chromatography, as follows.

The ion exclusion chromatography separation was carried out over a 15-day period with continuous operation except for periodic shutdowns for filter changes and one complete cycle of water flushing. The separation was carried out on an Improved Simulated Moving Bed (ISMB) system (Eurodia Industrie S.A. of Wissous, France, available through Ameridia, Somerset, N.J.) of volume 6700 liters, packed with cation exchange resin from Mitsubishi Chemical, resin #UBK530. The ISMB system consists of 4 columns with 4 bed shifts per cycle and was operated with the feed stream at pH 5.8 to 6.5. The system was maintained at 70° C. as was the process feed and the dilution water. The process stream was fed at an average rate of 262 liters per hour and dilution water was added at a rate of 969 L/hr, which is an average ratio of 3.7:1 with the process feed. Salt raffinate and sugar product streams were collected at average flow rates of 760 and 461 liters/hr, respectively.

The salt raffinate stream contained over 99% of the salt. The inorganic salt concentrations were 35.6 g/L sodium sulfate, 14.4 g/L potassium sulfate, 1.9 g/L magnesium sulfate. In addition, the organic salt acetate was present at a concentration of 3.3 g/L, measured as acetic acid. A very small fraction of the organic compounds were present in this stream at concentrations of 1.2 g/L glucose, 0.5 g/L xylose, 0.2 g/L arabinose, 0.3 g/L furfural and 0.6 g/L hydroxymethyl furfural.

The sugar product stream contained the vast majority of the organic compounds and tiny amounts of salt. The concentrations of this stream were 1.2 g/L sodium sulfate, 0.4 g/L potassium sulfate, 66 g/L glucose, 22 g/L xylose, 3.3 g/L arabinose, and 0.09 g/L acetic acid, measured as acetate salt.

The salt raffinate stream is evaporated to 40% solids, then sent to an evaporator-crystallizer to produce granulates for use as fertilizer.

Example 2

Recovery of Soluble Inorganic Salt from Wheat Straw Leachate

Wheat straw was received in bales measuring 3 feet by 3 feet by 4 feet. The wheat straw consisted of 15.9% moisture. The composition of the straw, on a dry basis, was 60.1% carbohydrates, 19.7% lignin, 3.36% protein, 3.0% silica, and 4.5% non-silica salts. The inorganic cationic salt ions included 1.28% potassium, 0.45% calcium, 0.04% sodium, and 0.15% magnesium. The inorganic anions were chloride at 0.22% and 0.04% phosphate. The organic salt oxalate was present at a concentration of 0.55%. A weight of 1199 kg wet straw was hammer-milled to ⅛ inch.

The hammer-milled straw was slurried in 49,590 liters of 65° C. water. The slurry was gravity fed into a mixed tank, where it was mixed overnight for 18 hours and maintained at 65° C. The pH was 6.4 throughout the leaching process. The slurry was then flowed through screened baskets by gravity to separate the solids from the liquid leachate stream. The screened baskets produced a cake of 21.1% solids content.

The leachate contained 9.9% of the initial fiber solids. This was at a concentration of 2010 mg/L total dissolved solids, which included 127 mg/L protein, 262 mg/L potassium, 1.5 mg/L calcium, 36 mg/L magnesium, 55 mg/L chloride and a majority of 1530 mg/L unidentified. Other than calcium, which was not removed to a significant degree, the salts were removed from the straw by leaching at a yield of 87% to 93%. The protein yield in the leachate was 14%.

The leachate stream was evaporated to increase the solids concentration approximately 100-fold, to a solids concentration of 19.9% and a volume of 464 liters. A significant amount of protein precipitated and was removed by filtration. A preliminary evaluation of drying and crystallizing the filtrate indicated that the inorganic salts constituted much too small a proportion of the total solids for crystallization of the salts to be possible.

An aliquot of the leachate stream is fed to a laboratory ion exclusion chromatography system to separate the salts from the organics. The ion exclusion chromatography separation is carried out on a fixed bed of volume 127 mL, packed with cation exchange resin from Mitsubishi Chemical, resin #UBK530. The bed is operated with the feed stream at pH 6.8. The column is maintained at 70° C. as is the feed and the elution water. Prior to carrying out the separation, the column is conditioned with three bed volumes of the process stream. The process stream is fed in a pulse of 5 mL and elution water is then added at a rate of 4 mL/minute. Salt raffinate and sugar product streams are collected as the conductivity of the effluent indicates the presence and absence of salt, respectively.

The salt raffinate stream contains most of the inorganic salts, which are primarily potassium chloride and magnesium chloride and a small amount of organic impurities. The inorganic salt concentrations are high enough to permit crystallization to recover the salts.

Example 3

Recovery of Soluble Inorganic Salts from Wheat Straw Leachate

Wheat straw was received in bales measuring 3 feet by 3 feet by 4 feet. The wheat straw consisted of 6.4% moisture. The composition of the straw, on a dry basis, was 60.3% carbohydrates, 18.7% lignin, 3.6% protein, 3.1% silica, and 4.9% non-silica salts. The inorganic cationic salt ions present included 1.22% potassium, 0.57% calcium, 0.04% sodium, and 0.15% magnesium. The inorganic anions were chloride at 0.10%, 0.16% phosphate and 0.08% sulfate. A weight of 3,363 kg of moist straw was hammer-milled to ⅛ inch pieces.

The hammer-milled straw was slurried in 70,626 liters of 65° C. water. The slurry was gravity fed into a mixed tank, where it was mixed overnight for 18 hours and maintained at 65° C. The pH was 4.9 throughout the leaching process. The slurry was then flowed through a centrifuge to separate the solids from the liquid leachate stream. The centrifuge produced a cake of 29.6% solids content.

The leachate contained 10.6% of the initial fiber solids. This was at a concentration of 4090 mg/L total dissolved solids, which included 1138 mg/L protein, 494 mg/L potassium, 67 mg/L calcium, 36 mg/L magnesium, 67 mg/L chloride, 80 mg/L of sulfate, 45 mg/L of phosphate, 27 mg/L of sodium, 163 mg/L of silica, 2010 mg/L of soluble phenolics and about 600 mg/L unidentified. Other than calcium and silica, which were not removed to a significant degree, the salts were removed from the straw by leaching at a yield of 50% to 93%. The protein yield in the leachate was 72%.

The leachate stream is evaporated to increase the solids concentration approximately 40-fold, to a solids concentration of 19.6% and a volume of 1770 liters. A significant amount of protein precipitates and is removed by filtration.

An aliquot of the leachate stream is fed to a laboratory ion exclusion chromatography system to separate the salts from the organics. The ion exclusion chromatography separation is carried out on a fixed bed of volume 127 mL, packed with cation exchange resin from Mitsubishi Chemical, resin #UBK530. The bed is operated with the feed stream at pH 6.8. The column is maintained at 70° C. as is the feed and the elution water. Prior to carrying out the separation, the column is conditioned with three bed volumes of the process stream. The process stream is fed in a pulse of 5 mL and elution water is then added at a rate of 4 mL/minute. Salt raffinate and sugar product streams are collected as the conductivity of the effluent indicates the presence of salt and water, respectively.

The salt raffinate stream contains most of the inorganic salts, which are primarily potassium chloride and magnesium chloride, and a small amount of organic impurities. The inorganic salt concentrations are high enough to permit crystallization to recover the salts.

Example 4

Recovery of Soluble Inorganic Salts during Conversion of Wheat Straw to Ethanol

A sugar hydrolyzate stream containing ammonium sulfate and other soluble inorganic salts was prepared as follows.

Wheat straw was received in bales measuring 3 feet by 3 feet by 4 feet and chopped and leached according to the procedures of Example 3. The leached wheat straw consisted of 57.1% carbohydrates, 36.6% lignin, 1.75% protein, 3.9% silica, and 0.8% non-silica salts. The salts included 0.2% potassium, 0.17% calcium, 0.05% sodium, 0.03% magnesium, <0.01% phosphate, 0.014% chloride and 0.023% sulfate. The leached straw was slurried in water at a ratio of 8 parts water to 1 part solids. The slurry was pumped through piping heated by direct injection with 350 psig steam to reach a temperature of 185° C. Once at this temperature, 10% concentrated sulfuric acid was added at a level of 0.9% acid on solids (w/w). The heated, acidified stock was held at this condition for 2 minutes as it passed through a pipe of 8 inches diameter. Upon exiting the pipe, the slurry was flashed through a series of three cyclones to drop the temperature to 75° C. and then cooled to 50° C. by using heat exchange with cool water. The slurry was then adjusted to pH 5.0 with concentrated ammonium hydroxide.

Upon acid addition, the soluble salts of potassium sulfate, sodium sulfate, and magnesium sulfate were formed. The insoluble salt, calcium sulfate, was also formed. Upon neutralization with ammonium hydroxide, which is soluble, the concentration of ammonium sulfate in the slurry increased markedly. The calcium sulfate concentration was above the solubility limit and a portion of it precipitated and deposited on the cyclones and related piping.

The neutralized, cooled pretreated slurry was then pumped into a hydrolysis tank at a volume of about 100,000 liters. The tank is equipped with side-mounted eductors to mix the slurry. The slurry consisted of 4.5% undissolved solids, and the undissolved solids consisted of 55% cellulose. Once the pretreated slurry was added to the hydrolysis tank, cellulase enzyme from *Trichoderma reesei* was added. The enzyme dosage was 35 mg protein per gram cellulose, which corresponded to a cellulase activity of 35.6 Filter Paper Units (FPU) per gram of cellulose.

The hydrolysis ran for 2 days, at which point over 90% of the cellulose was converted to glucose. The final glucose concentration was 26.0 to 28.0 g/L, with an average of 27.5 g/L. The hydrolysis slurry was pumped to a Lasta plate and frame filter press to separate the unhydrolyzed solid residue from the aqueous stream. A polyacrylamide flocculent was added at a level of 1-3 kg/t solids to aid in the filtration. The unhydrolyzed solid residue contains primarily lignin, unhydrolyzed cellulose and sand, but also the insoluble salts such as calcium sulfate. The aqueous process stream is essentially free of insoluble particles and contains glucose, xylose, and arabinose sugar; the soluble salts ammonium sulfate, potassium sulfate, magnesium sulfate and a small amount of dissolved calcium sulfate, and acetic acid, soluble lignin, and other dissolved organics.

The process stream was evaporated to increase the solids concentration three-fold by using a 4-effect falling film evaporator. The glucose concentration in the evaporated stream was 62 g/L, the xylose was 20 g/L, and the acetic acid was 2.0 g/L. The evaporated stream was filtered across the Lasta press with a Perlite filter aid to remove particulates.

The evaporated stream was pumped to a fermentor to carry out sugar fermentation with yeast. The yeast strain was LNHST from Purdue University and has been genetically modified to enable it to ferment xylose, as well as glucose, to ethanol. The strain was grown by propagation through successive fermentors, as described in U.S. Pat. No. 5,789,210. The fermentation was fed over a period of 7 hours and then run as a batch for 48 hours at a volume of 65,000 liters.

At the conclusion of the fermentation, the yeast cells were removed by centrifugation. The dilute beer was distilled to separate the ethanol from the aqueous solution. The distillation was carried out using a beer column and a rectifying column. The still bottoms were collected as a liquid stream from the bottom of the beer column with a volume of 87,000 liters.

The still bottoms were evaporated under vacuum at 80° C. to a volume of 18,000 liters with a solids concentration of 13%. Some of the solids precipitated upon evaporation. The pH of the evaporated slurry was adjusted to pH 7.0 with 30% ammonium hydroxide solution, and this caused more precipitation. The concentrated, pH-adjusted stream was sent to the Lasta press with a diatomaceous earth body feed to remove the precipitated solids. The clear, evaporated process stream had inorganic salt concentrations of 55 g/L ammonium sulfate, 20 g/L potassium sulfate, and 2.5 g/L magnesium sulfate. In addition, organic compounds present included 24 g/L xylose, 3.3 g/L arabinose, 3.4 g/L furfural, 3.5 g/L hydroxymethyl furfural, and 9.1 g/L acetate salt, an organic salt that was measured as acetic acid, and various trace metals (including trace quantities of calcium), and a significant amount of unidentified impurities.

The inorganic, soluble salts ammonium sulfate, potassium sulfate, and magnesium sulfate were recovered from the concentrated process stream by ion exclusion chromatography, as follows.

The ion exclusion chromatography separation is carried out over a 2.5-day period with continuous operation except for periodic shutdowns for filter changes and one complete cycle of water flushing. The separation is carried out on an Improved Simulated Moving Bed (ISMB) system (Eurodia Industrie S.A. of Wissous, France, available through Ameridia, Somerset, N.J.) of volume 6700 liters, packed with cation exchange resin from Mitsubishi Chemical, resin #UBK530. The ISMB system consists of 4 columns with 4 bed shifts per cycle and is operated with the feed stream at pH 6.0 to 7.5. The system is maintained at 65° C. as was the process feed and the dilution water. The process stream is fed at an average rate of 320 liters per hour and dilution water was added at a rate of 960 L/hr, which is an average ratio of 3.0:1 with the process feed. Salt raffinate and sugar product streams are each collected at average flow rates of 640 liters/hr.

The salt raffinate stream contains over 99% of the salt. The inorganic salt concentrations are 15.6 g/L ammonium sulfate, 4.4 g/L potassium sulfate, and 1.9 g/L magnesium sulfate. In addition, the organic salt acetate is present at a concentration of 0.9 g/L, measured as acetic acid. A very small fraction of the organic compounds were in this stream at concentrations of 0.5 g/L xylose, 0.2 g/L arabinose, 0.3 g/L furfural, and 0.6 g/L hydroxymethyl furfural.

The sugar product stream contained the vast majority of the organic compounds and very small amounts of salt. The concentrations of this stream were 1.2 g/L ammonium sulfate, 0.4 g/L potassium sulfate, 14 g/L xylose, 2.3 g/L arabinose, and 0.09 g/L acetic acid, measured as acetate salt.

The salt raffinate stream is evaporated to 40% solids, then sent to an evaporator-crystallizer to produce granulates for use as fertilizer.

All citations are hereby incorporated by reference herein in their entirety.

The present invention has been described with regard to one or more embodiments. However, it will be apparent to persons skilled in the art that a number of variations and modifications can be made without departing from the scope of the invention as defined in the claims.

We claim:

1. A method for processing a lignocellulosic feedstock and obtaining an inorganic salt selected from the group consisting of ammonium sulfate, potassium sulfate, ammonium phosphate and potassium phosphate during said processing, said method comprising:
    (a) pretreating the lignocellulosic feedstock by adding one or more than one soluble base selected from the group consisting of ammonia, ammonium hydroxide and potassium hydroxide to the lignocellulosic feedstock to produce a pretreated lignocellulosic feedstock;
    (b) optionally separating an aqueous stream from the pretreated lignocellulosic feedstock;
    (c) adding sulfuric acid or phosphoric acid to the pretreated lignocellulosic feedstock to adjust the pH of the pretreated lignocellulosic feedstock to produce a neutralized feedstock and inorganic salt selected from the group consisting of ammonium sulfate, potassium sulfate, ammonium phosphate and potassium phosphate;
    (d) hydrolyzing the neutralized feedstock to produce a hydrolyzed feedstock; and
    (e) recovering an inorganic salt comprising inorganic salt arising from step (c) from a salt-containing stream obtained during the processing of the lignocellulosic feedstock.

2. The method of claim 1, wherein the lignocellulosic feedstock is selected from the group consisting of corn stover, wheat straw, barley straw, canola straw, rice straw, oat straw, soybean stover, grass, switch grass, miscanthus, cord grass, reed canary grass, aspen wood, sawdust, bagasse and beet pulp.

3. The method of claim 1, wherein, in the step of recovering (step (e)), the inorganic salt is recovered by ion exclusion.

4. The method of claim 3, wherein the step of recovering (step (e)) is followed by crystallization of the inorganic salt, electrodialysis, drying, or agglomeration and granulation.

5. The method of claim 3, wherein the inorganic salt is concentrated by evaporation, membrane filtration, or a combination thereof, prior to recovery to produce a concentrated solution comprising the inorganic salt.

6. The method of claim 5, wherein the concentrated solution is clarified by microfiltration, plate and frame filtration, or centrifugation prior to recovery.

7. The method of claim 1, wherein the one or more than one soluble base is selected from the group consisting of ammonium hydroxide and ammonia.

8. The method of claim 7, wherein the step of pretreating (step (a)) is performed at a temperature from about 20° C. to about 200° C., at a pH from about pH 9.5 to about 12 and for a time period of from about 2 to about 20 minutes.

9. The method of claim 1, wherein the processing of the lignocellulosic feedstock further comprises:
    (f) fermenting the sugar stream to produce a fermentation broth comprising ethanol; and
    (g) distilling the fermentation broth to produce concentrated ethanol and a still bottoms stream.

10. The method of claim 9, wherein the salt-containing stream, from which the inorganic salt is recovered, is the still bottoms stream and wherein the inorganic salt so recovered is purified.

11. The method of claim 10, wherein, prior to the step of recovering the inorganic salt from the still bottoms, the concentration of the still bottoms is increased by evaporation, membrane filtration, or a combination thereof, to produce concentrated still bottoms, followed by a step of ion exclusion chromatography using a simulated moving bed (SMB) process.

12. The method of claim 11, wherein the concentrated still bottoms are clarified by microfiltration, plate and frame filtration or centrifugation, prior to the step of ion exclusion chromatography.

13. The method of claim 12, wherein the step of purifying the inorganic salt comprises crystallization of the inorganic salt, electrodialysis, drying, or agglomeration and granulation.

14. The method of claim 1, wherein, in the step of hydrolyzing (step (d)), one or more than one cellulase enzyme is added to the neutralized feedstock so that at least a portion of cellulose in the neutralized feedstock is hydrolyzed to produce glucose.

15. The method of claim 1, wherein, after the step of hydrolyzing (step (d)), the sugar stream is separated from the hydrolyzed feedstock to form a solid residue and a sugar hydrolyzate stream.

16. The method of claim 15, wherein the inorganic salt is concentrated by evaporation, membrane filtration, or a combination thereof.

17. The method of claim 1, wherein, in the step of hydrolyzing (step (d)), the neutralized feedstock is treated with one or more than one acid so that at least a portion of cellulose and hemicellulose in the neutralized feedstock is hydrolyzed to produce a sugar stream comprising glucose, xylose, arabinose, mannose and galactose.

18. The method of claim 1, wherein the inorganic salt is soluble.

19. The method of claim 1, wherein the inorganic salt is for use as a fertilizer.

20. The method of claim 1, wherein the salt-containing stream from which the inorganic salt is recovered, is the neutralized feedstock, the sugar stream, a still bottoms stream or a combination thereof.

21. The method of claim 20, wherein
    in the step of pretreating (step (a)), the one or more than one soluble base is ammonia, ammonium hydroxide, or a combination thereof;
    in the step of adding (step (c)), the one or more than one acid is sulfuric acid; and
    the inorganic salt that is recovered from the salt-containing stream is ammonium sulfate.

22. The method of claim 21, wherein, in the step of recovering (step (e)), the inorganic salt is recovered by ion exclusion.

23. The method of claim 22, wherein the step of recovering (step (e)) is followed by crystallization of the inorganic salt, electrodialysis, drying, or agglomeration and granulation.

24. The method of claim 21, wherein the step of pretreating (step (a)) is performed at a temperature from about 20° C. to about 200° C., at a pH from about pH 9.5 to about 12 and for a time period of from about 2 to about 20 minutes.

25. The method of claim 24, wherein the ammonium sulfate is for use as a fertilizer.

26. The method of claim 1, wherein the sugar stream is processed by fermenting the sugar stream to produce a fermentation broth comprising ethanol or butanol; and separating the ethanol or butanol from the fermentation broth to produce a stream comprising concentrated ethanol or butanol and an aqueous stream comprising the inorganic salt, wherein the salt-containing stream, from which the inorganic salt is recovered, is the aqueous stream comprising the inorganic salt produced during the step of separating the ethanol or butanol.

27. The method of claim 26, further comprising the steps of purifying the recovered inorganic salt to obtain a purified inorganic salt and producing a product comprising the purified inorganic salt.

28. The method of claim 27, wherein the step of purifying comprises performing ion exclusion chromatography, followed by electrodialysis, crystallization, drying, or agglomeration and granulation.

29. A method for processing a lignocellulosic feedstock and obtaining an inorganic salt selected from the group consisting of ammonium sulfate, potassium sulfate, ammonium phosphate and potassium phosphate, said method comprising:

(a) pretreating the lignocellulosic feedstock by adding one or more than one soluble base selected from the group consisting of ammonia, ammonium hydroxide and potassium hydroxide to the lignocellulosic feedstock to produce a pretreated lignocellulosic feedstock;

(b) separating an aqueous sugar-base mixture from solids contained in the pretreated lignocellulosic feedstock;

(c) neutralizing the sugar-acid mixture with sulfuric acid or phosphoric acid, thereby producing a neutralized aqueous stream comprising sugar and inorganic salt selected from the group consisting of ammonium sulfate, potassium sulfate, ammonium phosphate and potassium phosphate; and (d) recovering the inorganic salt from the neutralized aqueous stream.

30. The method of claim 29, wherein the lignocellulosic feedstock is selected from the group consisting of corn stover, wheat straw, barley straw, canola straw, rice straw, oat straw, soybean stover, grass, switch grass, miscanthus, cord grass, reed canary grass, aspen wood, sawdust, bagasse and beet pulp.

31. The method of claim 29, wherein, in the step of recovering (step (d)), the inorganic salt is recovered by ion exclusion.

32. The method of claim 31, wherein the step of recovering (step (d)) is followed by crystallization of the inorganic salt, electrodialysis, drying, or agglomeration and granulation.

33. The method of claim 31, wherein the inorganic salt is concentrated by evaporation, membrane filtration, or a combination thereof, prior to recovery to produce a concentrated solution comprising the inorganic salt.

34. The method of claim 33, wherein the concentrated solution is clarified by microfiltration, plate and frame filtration, or centrifugation prior to recovery.

35. The method of claim 29, wherein the one or more than one acid is sulfuric acid.

36. The method of claim 35, wherein the one or more than one alkali is selected from the group consisting of ammonium hydroxide and ammonia.

37. The method of claim 36, wherein the step of pretreating (step (a)) is performed at a temperature from about 20° C. to about 200° C., at a pH from about pH 9.5 to about 12 and for a time period of from about 2 to about 20 minutes.

* * * * *